(12) United States Patent
Lou et al.

(10) Patent No.: US 10,729,345 B2
(45) Date of Patent: Aug. 4, 2020

(54) DETECTION OF REGIONS EXHIBITING IRREGULAR ELECTROPHYSIOLOGICAL ACTIVITY

(71) Applicant: CARDIOINSIGHT TECHNOLOGIES, INC., Independence, OH (US)

(72) Inventors: Qing Lou, Solon, OH (US); Jeffrey B. Adair, Cuyahoga Falls, OH (US); Qingguo Zeng, Solon, OH (US); Ping Jia, Solon, OH (US); Ryan Bokan, Cleveland, OH (US); Connor Edel, Akron, OH (US); Rahsean Ellis, Intercession City, FL (US); Brian P. George, Cleveland, OH (US); Raja Ghanem, Ladera Ranch, CA (US); Timothy G. Laske, Shoreview, MN (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 90 days.

(21) Appl. No.: 15/971,559

(22) Filed: May 4, 2018

(65) Prior Publication Data
US 2019/0336023 A1    Nov. 7, 2019

(51) Int. Cl.
*A61B 5/04* (2006.01)
*A61B 5/044* (2006.01)

(52) U.S. Cl.
CPC .......... *A61B 5/04012* (2013.01); *A61B 5/044* (2013.01); *A61B 5/04011* (2013.01)

(58) Field of Classification Search
CPC .. A61B 5/04012; A61B 5/04011; A61B 5/044
See application file for complete search history.

(56) References Cited

U.S. PATENT DOCUMENTS 5,487,391 A    1/1996 Panescu
6,301,496 B1 * 10/2001 Reisfeld ............ A61B 5/04011
                                                    345/419

(Continued)

FOREIGN PATENT DOCUMENTS

WO    2000/046689 A1    8/2000

OTHER PUBLICATIONS

Applicant: CardioInsight Technologies, Inc.; PCT International Patent Application No. PCT/US2019/018321; Filed: Feb. 15, 2019; International Search Report and Written Opinion; 11 pgs.

*Primary Examiner* — Amanda K Hulbert
*Assistant Examiner* — Natasha Patel
(74) *Attorney, Agent, or Firm* — Tarolli, Sundheim, Covell & Tummino LLP

(57) ABSTRACT

For example, one or more non-transitory computer-readable media includes executable instructions to perform a method. The method includes defining a plurality of spatial regions distributed across a geometric surface. At least one wave front that propagates across the geometric surface is detected based on electrical data representing electrophysiological signals for each of a plurality of nodes distributed on the geometric surface over at least one time interval. An indication of conduction velocity of the wave front is determined for at least one spatial region of the plurality of spatial regions during the time interval based on a duration that the wave front resides within the at least one spatial region. Slow conduction activity is identified for the at least one spatial region based on comparing the indication of conduction velocity relative to a threshold. Conduction data is stored in memory to represent each slow conduction event.

30 Claims, 9 Drawing Sheets

(56) References Cited

U.S. PATENT DOCUMENTS

| | | |
|---|---|---|
| 2013/0131529 A1 | 5/2013 | Jia et al. |
| 2017/0003332 A1 | 1/2017 | George et al. |
| 2017/0055864 A1* | 3/2017 | Han .................. A61B 5/04011 |
| 2017/0185740 A1 | 6/2017 | Seegerer et al. |
| 2019/0246930 A1* | 8/2019 | Zhu ..................... A61B 5/0422 |

* cited by examiner

DETECTION OF REGIONS EXHIBITING IRREGULAR ELECTROPHYSIOLOGICAL ACTIVITY

TECHNICAL FIELD

This disclosure relates to detection of regions exhibiting irregular electrophysiological activity.

BACKGROUND

Electrocardiographic mapping (ECM) is a technology that is used to determine and display heart electrical information from sensed electrical signals. ECM can be performed based on invasive or non-invasive measurements of cardiac electrical activity.

Electrophysiology data can be used in the diagnosis and treatment of cardiac arrhythmias.

SUMMARY

In one example, one or more non-transitory computer-readable media having instructions executable by a processor can perform a method. The method includes defining a plurality of spatial regions distributed across a three-dimensional geometric surface corresponding to a patient's heart. At least one wave front that propagates across the geometric surface is detected based on electrical data representing electrophysiological signals for each of a plurality of nodes distributed on the geometric surface over at least one time interval. An indication of conduction velocity of the wave front is determined for at least one spatial region of the plurality of spatial regions during the time interval based on a duration that the wave front resides within the at least one spatial region. Slow conduction activity is identified for the at least one spatial region based on comparing the indication of conduction velocity relative to a threshold. Conduction data can be stored in memory to represent each slow conduction event.

Another example can provide a system that includes memory and at least one processor. The memory stores machine readable instructions and data, the data including electrical data representing electrophysiological signals for a plurality of nodes distributed across a geometric surface over at least one time interval. The processor can access the memory and execute the instructions. The instructions include code to detect at least one wave front that propagates across the geometric surface based on the electrical data, the geometric surface including a plurality of spatial regions. The instructions also include code to determine an indication of conduction velocity of the wave front for at least one spatial region of the plurality of spatial regions during the time interval based on a duration that the wave front resides within the at least one spatial region. The instructions also include code to identify a slow conduction event for the at least one spatial region based on comparing the indication of conduction velocity relative a threshold. Code can also store conduction data in the memory to represent each slow conduction event.

In another example, one or more non-transitory computer-readable media having instructions executable by a processor can perform a method. The method can include determining a cycle duration for at least one time interval of electrophysiological signals at each of a plurality of nodes distributed across an anatomical surface. Each cycle duration is compared to at least one threshold to identify each short duration event for each signal. A number of short duration events that occur during the time interval is quantified at each of the plurality of nodes. A graphical map can be generated to display the number of short duration events that occur spatially across a graphical representation of the anatomical surface.

Yet another example can provide a system that includes memory and at least one processor. The memory can store machine readable instructions and data, the data including electrical data representing electrophysiological signals for a plurality of nodes distributed across an anatomical surface over at least one time interval. The processor can access the memory and execute the instructions. The instructions include code to select at least one measurement time interval such that the electrophysiological signals for at least some of the plurality of nodes include fibrillatory signals. The instructions also include code to determine a cycle duration for the electrophysiological signals at each of the plurality of nodes over the at least one measurement time interval. The instructions also include code to compare each cycle duration to a threshold to identify short duration events for each the electrophysiological signals. The instructions also include code to quantify a number of short duration events at each of the plurality of nodes that occur during the at least one measurement time interval. The instructions also include code to generate a graphical map visualizing the number of short duration events across a graphical representation of the anatomical surface.

DETAILED DESCRIPTION

Figure 1:
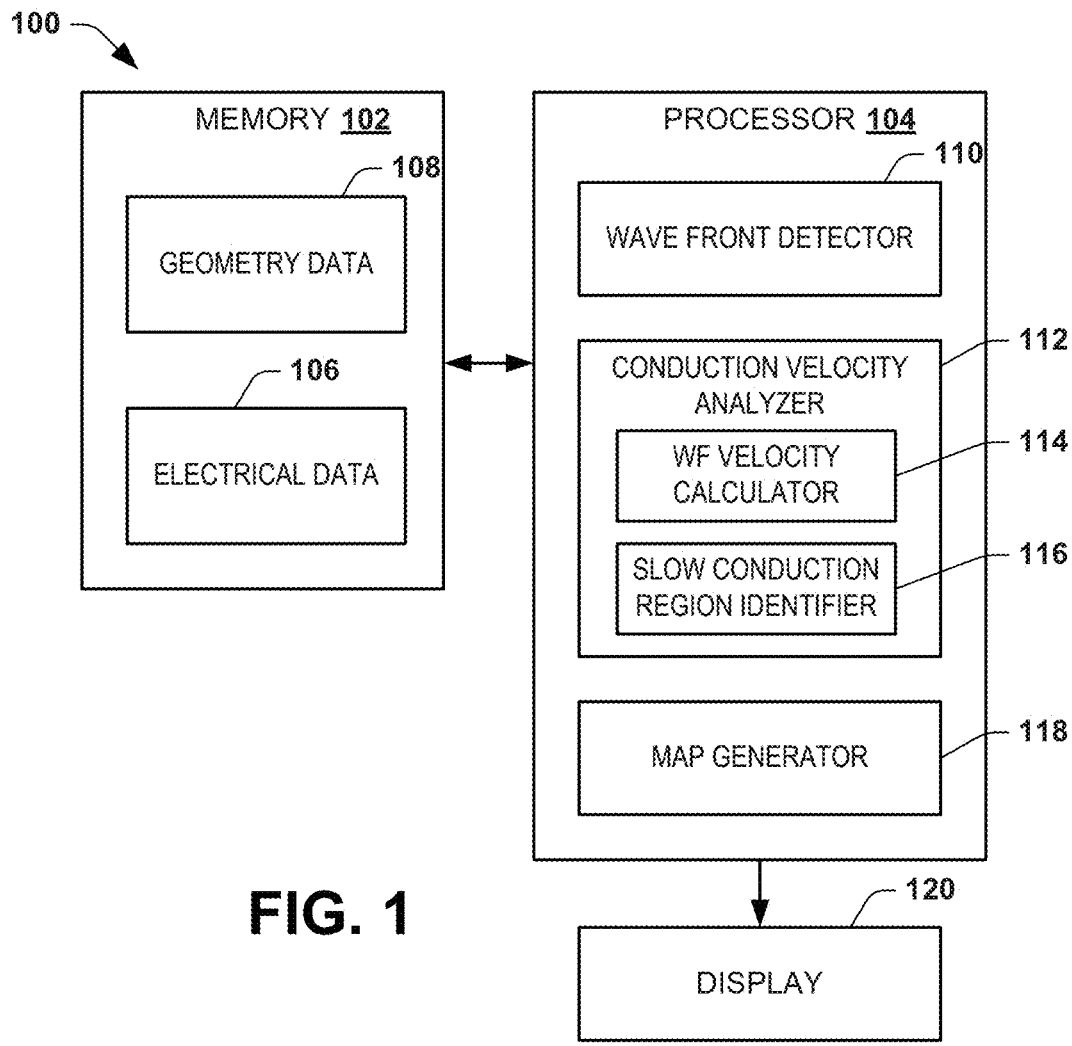
FIG. 1 depicts an example of a system to identify regions of slow conduction velocity.

This disclosure relates to detection of regions of tissue exhibiting certain irregular electrophysiological activity.

The irregular electrophysiological activity may include slow conduction (e.g., slower than a conduction threshold) of electrophysiological signals across the tissue. Additionally or alternatively, the irregular electrophysiological activity may include short duration events for the tissue. In some examples, the electrophysiological signals are analyzed during one or more time intervals of fibrillation (e.g., atrial and/or ventricular fibrillation) to determine and quantify the irregular electrophysiological activity. One or more corresponding graphical maps may be generated to visualize the irregular electrophysiological activity. In some examples, the detected irregular electrophysiological activity is computed for each spatial region as relative value to facilitate visualization thereof (e.g., by mapping the values to a defined color scale).

As one example, a plurality of regions across a geometric surface (e.g., a three-dimensional cardiac surface) are defined. One or more wave fronts that propagate across the surface are detected over one or more time interval. An indication of conduction velocity of the wave front can be determined for at least some of the spatial regions. The indication of conduction velocity for a given wave front may be calculated, for example, as an average conduction velocity of the given wave front for each respective region through which the given wave front propagates. As an example, since the size of the regions may be known, the average conduction velocity of the wave front for a respective spatial region may be determined as a function of the region's size and the time interval during which such wave front resides within the respective spatial region. For example, slow conduction activity for one or more spatial region thus may be identified if the determined indication of conduction velocity for a given wave front through the region is below a prescribed slow conduction threshold. As yet another example, slow conduction activity for one or more spatial region thus may be identified if when a propagating wave front remains (e.g., continuously) within a particular spatial region for at least some minimum amount of time. The indication of conduction velocity may be stored in memory as conduction data representing each slow conduction event.

As another example, a fibrillatory cycle duration may be determined for electrophysiological signals, which are exhibiting fibrillatory behavior, at each of a plurality of nodes over a time interval. Each fibrillatory cycle duration may be compared to a cycle duration threshold to identify each short duration event that occurs during each signal. The number of short duration events at each of the plurality of nodes that occur during the time interval may be quantified and stored in memory. As mentioned, a graphical map may be generated based on the number short duration events to visualize an extent to which each region exhibits such short duration relative other regions.

While many examples of wave front detection are disclosed with respect to reconstructed electrograms on a cardiac envelope or cardiac surface, the system and method disclosed herein are equally applicable to any electrical signals for a geometric surface, whether measured directly from a surface or derived from measurements. This concept can be applied on ECG and EGM potentials. Moreover, while many examples herein are described in the context of wave front detection and mapping of cardiac electrical signals, it is to be understood that the approaches disclosed herein are equally applicable to other electrophysiological signals, such as electroencephalography, electromyography, electrooculography and the like.

FIG. 1 depicts an example of a system 100 to detection one or more regions of irregular electrophysiological activity of tissue, such as corresponding to the heart or other tissue. In the example of FIG. 1, the system 100 is demonstrated as a computing apparatus that includes a memory 102 and one or more processor 104. The memory 102 is configured as one or more non-transitory media to store data and instructions. The processor 104 is configured to access the memory and execute the instructions to perform the methods and functions disclosed herein.

The memory 102 stores electrical data 106 such as representing electrical signals at plurality of locations (nodes) distributed across a three-dimensional (3D) surface envelope over one or more time intervals. The electrical data 106 may include real-time measurements of the electrical activity and/or previous measurements, which generally may vary depending on whether the system 100 is being utilized for real time analysis (e.g., during an electrophysiological study) or post-procedure analysis. In one example, the electrical data 106 may be measured at the locations invasively from the surface of the heart (e.g., via a lead or a basket catheter from an endocardial and/or epicardial surface). The invasive measurements may be based on contact with the tissue or the measurements may be obtained in a non-contact manner. In another example, the electrical data 106 may be reconstructed onto the 3D surface geometry of the based electrical signals measured non-invasively (e.g., by an arrangement of body surface electrodes) by computing a solution to the inverse problem. In yet other examples, the electrical data 106 can include or be derived from a hybrid approach that includes both non-invasively acquired electrical signals and invasively acquired electrical signals. The system 100 thus may be implemented regardless of how the electrical data is obtained.

The memory 102 also stores geometry data 108 representing geometry of the three-dimensional surface. As one example, the 3D surface corresponds to a three dimensional epicardial surface geometry of a heart. As another example, the 3D surface can correspond to a three dimensional endocardial surface geometry of the heart. As yet another alternative example, such as where the electrical data 106 represents reconstructed electrical activity on the 3D surface, the 3D surface may correspond to virtually any geometric surface that resides between a region inside the patient's heart and the outer surface of the patient's torso where electrical measurements are non-invasively acquired. The geometry data 108 thus may correspond to actual patient anatomical geometry, a preprogrammed generic model or a combination thereof (e.g., a model that is modified based on patient anatomy).

As an example, the geometry data 108 may be derived from processing image data acquired for the patient via an imaging modality (not shown). For example, the imaging system 130 can be implemented according to any imaging modality, such as computed tomography (CT), magnetic resonance imaging (MRI), x-ray, fluoroscopy, ultrasound or the like, to acquire three-dimensional image data for the patient's torso. Such image processing can include extraction and segmentation of anatomical features, including one or more organs and other structures, from a digital image set.

Figure 3:
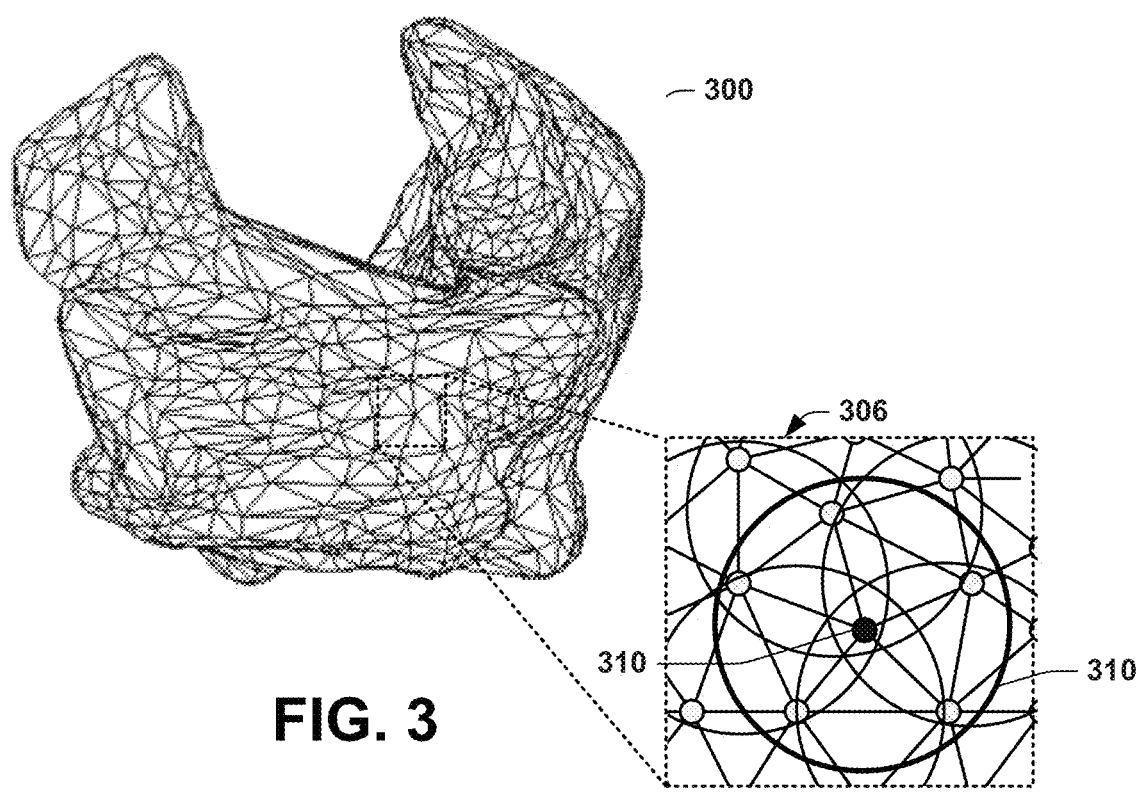
FIG. 3 depicts an example of a mesh of an anatomical surface showing a plurality of regions across part of the surface.

The geometry data 108 may also define a plurality of spatial regions across the 3D surface. As an example, the processor 104 is programmed to process geometry surface data and divide the surface into plurality of spatial regions distributed across the 3D surface corresponding to a patient's heart. Each of the spatial regions may be the same size or be different known sizes, for example. As an example, the 3D geometric surface may be in the form of a 3D surface mesh, such as shown in FIG. 3, which includes a plurality of nodes that are interconnected to each adjacent node by an edge of a meshed surface. Thus, the electrical data from which the wave fronts are detected correspond to electrical signals at each of the plurality of nodes. As mentioned, the electrical signals can be unipolar signals reconstructed to each of the nodes from electrical signals measured non-invasively from a body surface.

In one example, each of the plurality of spatial regions is defined as a circular region having a predetermined radius around a respective central node (e.g., the node is at the center of the region), thus providing each spatial region as having a predetermined diameter. The radius thus may be set to be greater than the distance between nodes, such that the spatial regions overlap with adjacent spatial regions. In some examples, a spatial region may include a central node as well as a set of two or more neighboring adjacent nodes. In another example, the spatial regions may be configured to be non-overlapping (e.g., boundaries of adjacent regions are aligned spatially to abut or be spaced apart from each other).

The processor 104 is configured to execute machine-readable instructions, demonstrated in the example of FIG. 1 as including a wave front detector 110, a conduction velocity analyzer 112 and a map generator 118. The wave front detector 110 is programmed to detect one or more wave fronts that propagate across the geometric surface based on electrical data 108 representing electrophysiological activity for each of a plurality of nodes distributed on the geometric surface over one or more time intervals. An example approach for wave front detection that the detector 110 may utilize to detect and track propagation of wave fronts is disclosed in U.S. Patent Pub. No. 20140200822, filed Jan. 14, 2014, and entitled WAVE FRONT DETECTION FOR ELECTROPHYSIOLOGICAL SIGNALS, which is incorporated herein by reference in its entirety. Thus, for each time frame (e.g., each time index during the one or more time intervals) the wave front detector 110 specifies the location of the wave front on the geometric surface, including locations of the ends of the wave front and the intermediate portion that extends between the ends thereof.

The conduction velocity analyzer 112 is programmed to identify slow conduction regions on the surface geometry. In this example, the term slow is used to indicate that the indication of conduction velocity is below an expected conduction velocity. The analyzer 112 includes a wave front velocity calculator 114 to determine an indication of conduction velocity of each wave front as it propagates through one or more spatial regions. The size of the spatial regions may be fixed or be a user-programmable parameter to define the resolution for determining the indication of conduction velocity. For example, the calculator 114 determines the indication of conduction velocity for each wave front in each spatial region based on a duration that each such wave front resides within a respective spatial region.

As a further example, the conduction velocity analyzer 112 includes a slow conduction region identifier 116 that is programmed to identify slow conduction activity for each spatial region based on the indication of conduction velocity (e.g., determined by the calculator 114) being less than a slow conduction threshold. For example, the slow conduction region identifier 116 provides an indication of slow conduction velocity that quantifies slow conduction for each of the plurality of spatial regions according to an amount of time that each wave front exhibits a predetermined amount of conduction velocity in each respective region that is slower than a threshold velocity. The quantified measure of slow conduction velocity for each spatial region may be stored in the memory 102 as conduction data.

The map generator 118 is programmed to generate a graphical map visualizing each region exhibiting a slow conduction event during the time interval on a graphical representation of the geometric surface corresponding to the heart based on the conduction data. The system 100 may also include a display (e.g., a screen, wearable augmented reality glasses, a heads up display or the like) 120 configured to display the graphical map that is produced. Thus, the graphical map may visualize the relative amount of slow conduction activity for each of the plurality of regions based on the conduction data.

Figure 2:
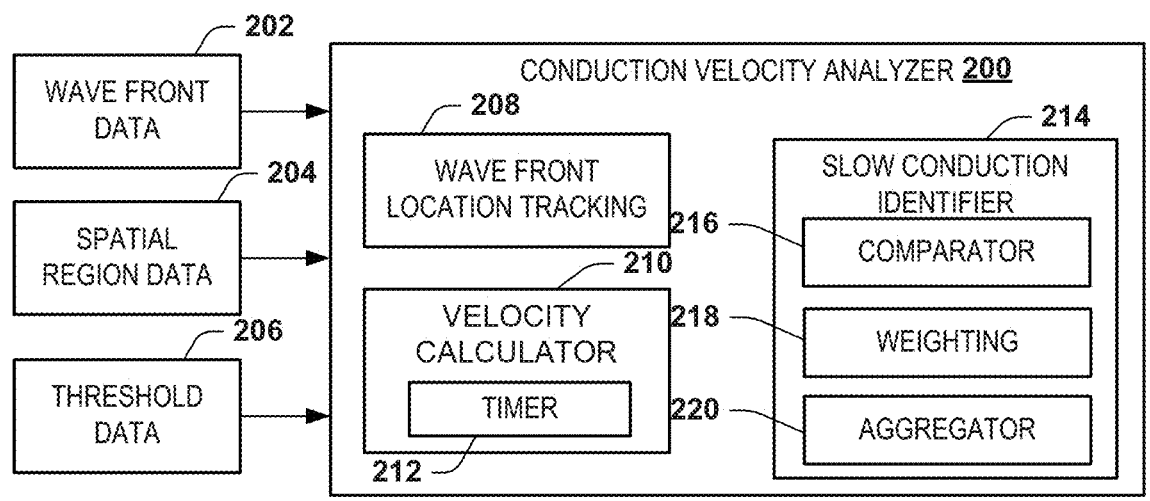
FIG. 2 depicts an example of a conduction velocity analyzer.

FIG. 2 depicts an example of a conduction velocity analyzer 200 that may be implemented to determine a spatial distribution of slow conduction events across a cardiac surface, which may be the entire surface or one or more parts (e.g., atria and/or ventricles). In this example, the analyzer 200 receives as inputs wave front data 202, spatial region data 204 and one or more conduction velocity thresholds 206. The wave front data 202 describes the location of one or more wave fronts as they propagate across a 3D surface over one or more time intervals. In one example, the wave front data 202 is produced by a wave front detector (e.g., detector 110) such as disclosed in the above-incorporated U.S. Patent Pub. No. 20140200822. In other examples, the wave front data may be provided according to other approaches. The spatial region data 204 define a plurality of spatial regions distributed across the 3D surface of the heart. The spatial regions may be the same size or different known sizes, and the size of the spatial regions sets a resolution for the conduction velocity mapping. As mentioned, in some examples, each of the plurality of spatial regions is defined as a circular region centered around a respective node on the 3D surface and having a predetermined fixed diameter. As one example, the diameter is less than or equal to about 5 cm (e.g., approximately 3 cm). The diameter may be user programmable in response to a user input.

The threshold data 206 sets a conduction velocity threshold to define wave front conditions used to identify slow conduction within each spatial region. As one example, the threshold may be set according to accepted slow conduction velocity levels, e.g., corresponding to about 40 cm/s. In another example, the threshold may be user programmable in response to a user input, such as to set one or more slow conduction thresholds.

The conduction velocity analyzer 200 includes a wave front tracking function 208. The tracking function 208, for example, tracks the location of each wave front across the 3D surface and, in particular, identifies one or more spatial regions across the 3D surface in which each respective wave front resides in each time frame (e.g., a time index). For instance, given a sample rate (e.g., 1 ms) for the electrical signals at each of the nodes, the wave front tracking function 208 can determine the location of the wave front for each time index (e.g., every 1 ms) over a time interval. The wave front thus may extend through a plurality of regions in each time frame, and the wave front tracking function 208 identifies each spatial region that the wave front resides in over a plurality of consecutive time frames. In examples, where the spatial region is defined as a surface area within a predetermined distance (e.g, a radius) from a central node, tracking function 208 can determine a wave front to reside within the given spatial region so long as a portion of the wave front is within the predetermined distance (e.g., determined as a Euclidean or other distance) from the central node.

A velocity calculator 210 determines an indication of conduction velocity for each wave front in each of the respective spatial regions. The velocity calculator 210 includes a timer 212 to determine a duration that each wave front spends in each of the spatial regions. For example, the timer 212 is configured to determine the duration for each wave front as a continuous duration of consecutive time frames during which each respective wave front resides in a given spatial region (e.g., based on the location information from the wave front tracking function 208). Thus, while the conduction velocity of each wave front may vary spatially and temporally in different parts of the wave front (e.g., from time frame to time frame) and within a given spatial region, the approach disclosed herein does not require that an instantaneous conduction velocity be calculated for any part of the wave front. Instead, in some examples, the velocity calculator 210 determines the indication of conduction velocity as an average conduction velocity.

As an example, the velocity calculator 210 determines the average conduction velocity for a given wave front as a function of the known spatial size of each region and the duration that the given wave front resides within each respective region. For example, assuming that a spatial region has a size of 3 cm and a wave front remains in the spatial region for a duration 82 ms (e.g., timer 212 tracks a portion of the given wave front within the spatial region for 82 consecutive 1 ms time frames), the conduction velocity of such wave front in the spatial region would be about 36.6 cm/s.

As another example, where the size of the spatial regions is the same and fixed across the 3D surface, instead of computing the indication of conduction velocity as a velocity value (e.g., distance/time), the velocity calculator 210 may determine the indication of conduction velocity for each spatial region as a time value corresponding to the duration that the given wave front resides (e.g., continuously) within each respective spatial region. Thus, in the above example, the indication of conduction velocity would be a duration 82 ms, as provided by the timer 212

A slow conduction identifier 214 is programmed to identify slow conduction velocity activity for each of the spatial regions. The slow conduction identifier 214 can employ a comparator 216 to compare the indication of conduction velocity of a given wave front for each spatial region relative to the threshold 206 to ascertain whether exhibits slow conduction velocity. Continuing with the above example, given a conduction velocity threshold of 40 cm/s, a determined conduction velocity of about 36.6 cm/s which would specify slow conduction region. In examples where the indication of conduction velocity is determined as a time value, the threshold 206 also may be provided a time value, such that a slow conduction region can be identified in response to determining that a given wave front resides within a spatial region for a duration of time that exceeds the time threshold. In the above example, for a circular spatial region having a 3 cm diameter the 40 cm/s threshold corresponds to a time threshold of 75 ms, such that the duration of 82 ms exceeds the time threshold and thereby indicates slow conduction activity for such region.

Additionally, by using duration within a spatial region as the indication of conduction velocity, the slow conduction identifier 214 may provide a measure for the extent of identified slow conduction activity. For example, the slow conduction identifier 214 includes a weighting function 218 that weights the duration of time that each wave front spends within each respective spatial region. For example, the weighting function 218 applies weights to each of the plurality of spatial regions (e.g., a weight value stored in a data record for the central node of each region) according to an amount of time that each wave front duration exceeds the threshold for each respective region. In examples where duration within a spatial region is utilized as the indication of conduction velocity, the weighting function 218 of the slow conduction region identifier 214 can subtract the threshold (e.g., a time value) from the duration that the wave front resides within a given spatial region to provide a weighted value to quantify the slow conduction activity for the given spatial region. For example, a duration of 82 ms provides a weighting value of 7 (e.g., equal to the difference between the duration and the time threshold of 75 ms).

The slow conduction identifier may repeat the comparing and weighting functions 216 and 218 based on the indication of conduction velocity provided for each of the remaining wave fronts and for each of the time interval(s) being analyzed. An aggregator 220 thus can aggregate the weighted values for each of the wave fronts detected in each the plurality of spatial regions and provide an aggregate weighted value to quantify a relative amount of slow conduction activity for each of the plurality of spatial regions over time, which may be stored in memory for further processing (e.g., mapping, diagnosis, treatment, etc.) as disclosed herein.

FIG. 3 depicts an example of mesh structure 300 demonstrating an example 3D surface of a heart. In this example, the surface is an epicardial surface of the entire heart. In other examples, different surfaces may be used. The mesh structure 300 includes nodes at intersections of edges of the mesh (e.g., a triangular mesh structure). As disclosed herein, the nodes correspond to locations on the surface where electrical signals (e.g., electrical potentials) are measured (e.g., directly or via inverse reconstruction). Shown in an enlarged view at 306, a plurality of circular spatial regions 308 are shown superimposed over a portion of the mesh. In this example, each of the spatial regions 308 includes a node 310 located at the center of the region, demonstrated for region 308 and node 310. Additionally, the spatial regions overlap with one or more other adjacent regions. In other examples, spatial regions 308 may not overlap or overlap with different amounts, generally depending on the distance between nodes and the size set for each of the spatial regions.

Figure 4:
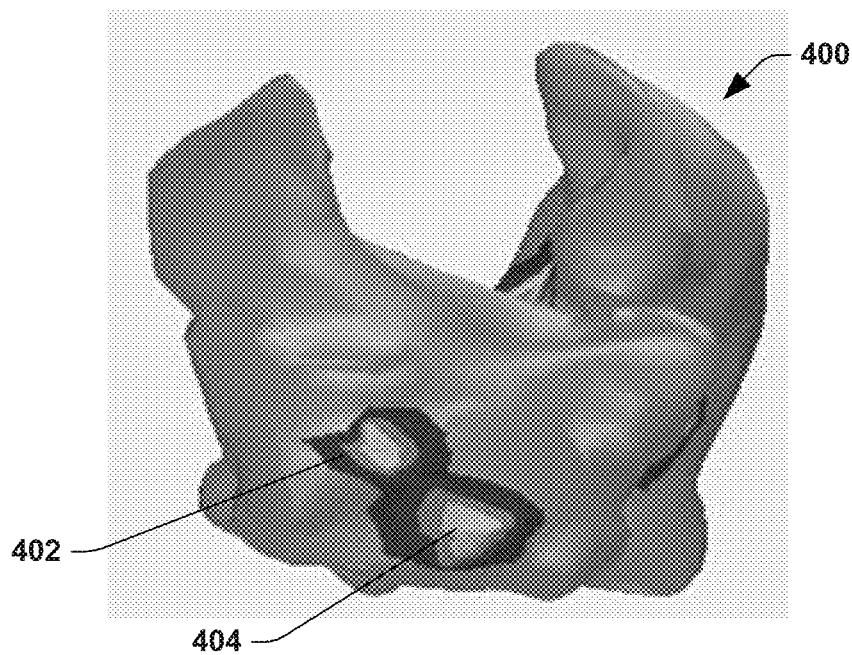
FIG. 4 depicts an example of a graphical map showing slow conduction regions across a surface.

FIG. 4 is an example of graphical map of a heart surface 400 that may be generated (e.g., by map generator 118). The map 400 provides a view of the heart surface to visualize slow conduction regions 402 and 404 on a display (e.g., display 120) or other output device. The slow conduction regions 402 and 404 may be identified from analysis of conduction velocity of wave fronts (e.g., by conduction analyzer 112, 200) across the heart surface over one or more time intervals, such as disclosed herein. The identified slow conduction regions 402 and 404 thus can be used as treatment sites (e.g., via a delivery device) or trigger further analysis to determine an appropriate course of treatment.

In view of the foregoing structural and functional features described herein, examples of methods that can be implemented will be better appreciated with reference to FIGS. 5, 6, 11 and 12. While, for purposes of simplicity of explanation, the methods are shown and described as executing serially, it is to be understood and appreciated that such method is not limited by the illustrated order, as some aspects could, in other embodiments, occur in different orders and/or concurrently with other aspects from that shown and described herein. Moreover, not all illustrated features may be required to implement a method. Each method or relevant portions thereof can be implemented as instructions stored in one or more non-transitory storage media as well as be executed by a processing resource (e.g., one or more processor cores) of a computer system, for example.

Figure 5:
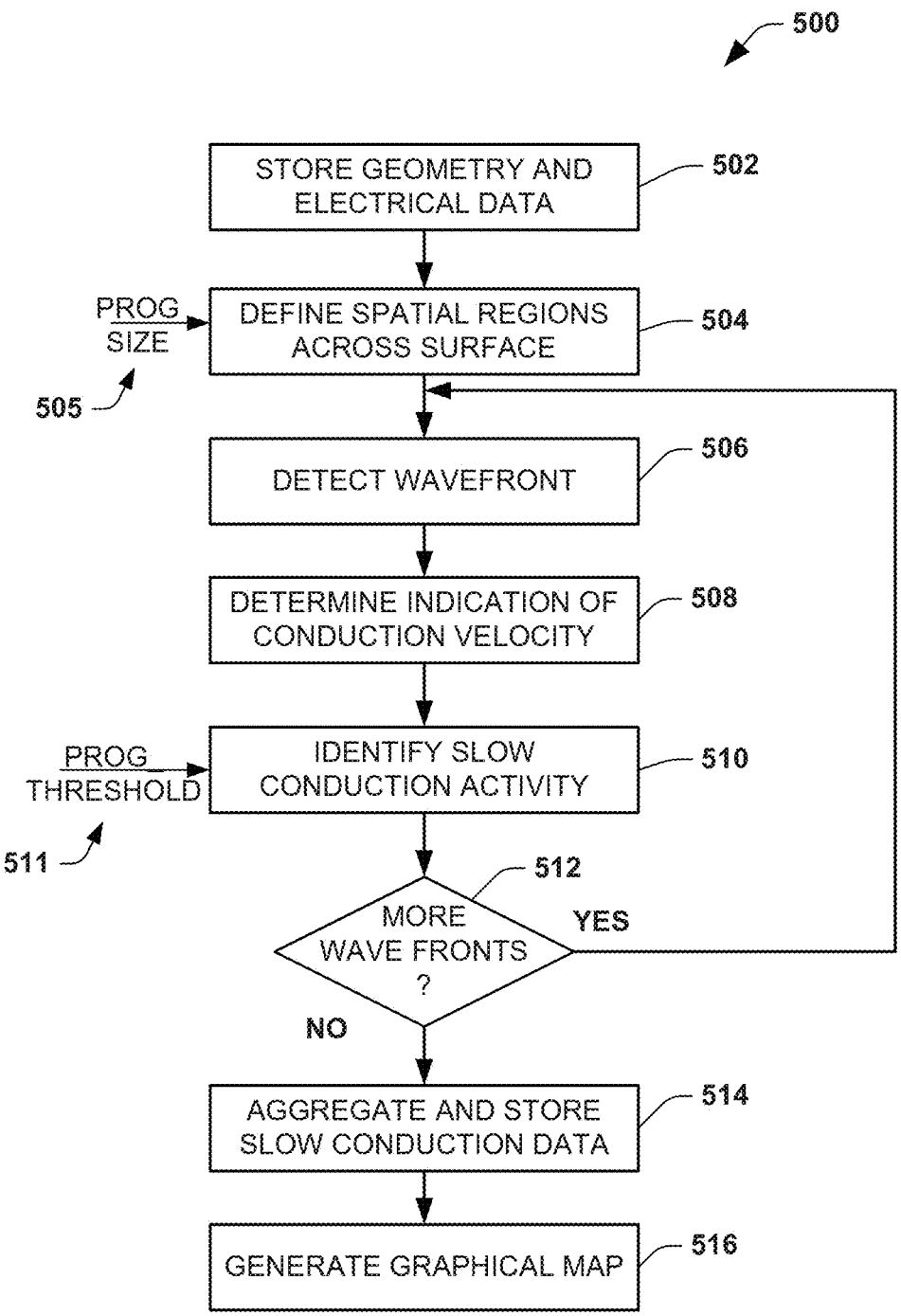
FIG. 5 is a flow diagram illustrating an example method that can be implemented to identify regions of slow conduction velocity.

FIG. 5 is a flow diagram depicting an example of a method 500 to identity slow conduction regions across an anatomical surface, such as the heart. The method 500 begins at 502 in which geometry and electrical data is stored (e.g., data 106, 108). At 504 spatial regions are defined across the surface. The size of the spatial region may be fixed or may be programmed in response to user input, demonstrated at 505. For instance, a user can program the size of the spatial regions to provide a desired resolution with respect to the surface on which the electrical activity has been determined. The spatial regions may be distributed across a 3D mesh structure, which includes a plurality of nodes connected together by edges to provide the mesh structure, such as corresponding to the anatomical surface that is described by the geometry data stored at 502. As one example, the spatial regions may be defined to cover an area of the surface that is within a predetermined distance of each of the nodes.

At 506 a wave front is detected. For example, the wave front is detected across the 3D surface based on analysis of electrical signals at the plurality of nodes on the surface (e.g., by wave front detector 110). For the detected wave front, at 508, an indication of conduction velocity is determined (e.g., by calculator 114, 210). As mentioned, the indication of conduction velocity may be determined as a velocity value (distance per unit time) or as a time value, which may vary depending on how the spatial regions defined at 504. For example, where spatial regions are sized uniformly (e.g., a fixed distance from each of the nodes), a duration that a wave front resides in each spatial region can provide an indication of average velocity.

At 510, slow conduction activity is identified based on an evaluation of the indication of conduction velocity. For example, the slow conduction activity may be identified based on comparing the indication of conduction velocity to a threshold. The threshold may be fixed or, in other examples, the threshold may be programmable in response to a user input, as demonstrated at 511. For example, a user may adjust a threshold to determine and localize regions exhibiting slower (or faster) conduction velocity relative to other regions, such as to see how conduction velocity may differ over the surface.

At 512, a determination is made as to whether there may be any additional wave fronts exist for which conduction velocity analysis is to be performed. If there are more wave fronts, the method returns to 506 to repeat the wave front detection for a corresponding time interval of electrical data for the anatomical surface, and further to determine conduction velocity and to identify slow conduction activity for each additional wave front in the time interval.

Once all of the wave fronts (e.g., detected at 506) have been analyzed, the method proceeds from 512 to 514. At 514, the slow conduction activity data is aggregated and stored as slow conduction data. At 516, a graphical map can be generated based on the slow conduction data, such as to visualize slow conduction activity that was detected across the surface of the heart over one or more time intervals (see, e.g., map 400 in FIG. 4).

Figure 6:
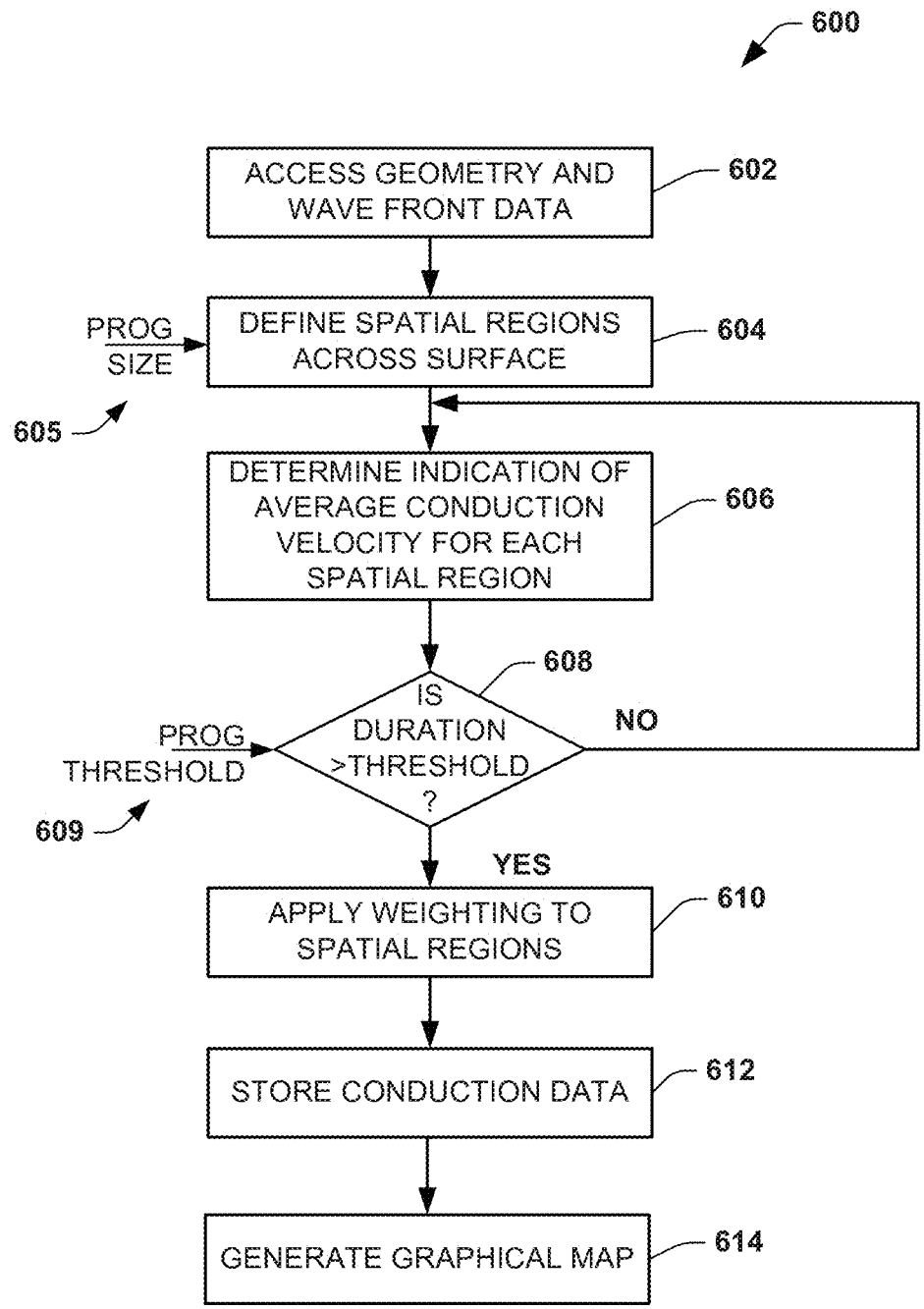
FIG. 6 is a flow diagram illustrating another example method that can be implemented to identify regions of slow conduction velocity.

FIG. 6 is a flow diagram depicting another example method 600 for identifying slow conduction velocity activity across an anatomical surface (e.g, a hear surface). The method begins at 602 in which geometry and wave front data is accessed from memory (e.g., memory 102). At 604, spatial regions across the surface are defined. The spatial regions can have a fixed predetermined size or, in other examples, have different sizes distributed across the surface. The size may be set in response to a user input demonstrated at 605, which may be used to set a resolution for the slow conduction velocity data.

At 606, an indication of average conduction velocity for each spatial region is determined. In this example, the average indications conduction velocity is computed for a given spatial region according to the duration that each wave front propagates through the given spatial region. At 608, a determination is made as to whether the determined indication of average conduction velocity exceeds a threshold. The threshold may be a default value or it may be programmable, such as in response to the user input demonstrated at 609. In some examples, the conduction velocity threshold may be set based upon an average conduction velocity derived from evaluating conduction velocity across the surface over a time period. In other examples, the threshold may be set based on empirical data or a generally accepted value for slow conduction velocity. The threshold that is applied at 608 may further be adjusted (e.g., normalized) based on and the size of each of the spatial regions, as defined at 604. If the indication of average conduction velocity does not exceed a threshold, the method can return to 606 to determine the indication of the average conduction velocity for the next spatial region. In this way, the method 600 may analyze the conduction velocity of each wave front across each spatial region, which can be compared to a corresponding threshold to identify slow conduction regions across the surface.

For each indication of conduction velocity that is determined to exceed the threshold at 608, the method proceeds to 610 to apply weightings to the spatial regions. The weightings are applied to further quantify the amount of slow conduction activity. For example, an amount of time that the wave front resides within a given spatial region beyond the threshold time can be applied to weight a central node of the given spatial region. By accumulating the weight values for wave fronts that propagate slowly through the spatial region over one or more time intervals, a relative measure of slow conduction velocity for each of the spatial regions may be spatially linked with the nodes and stored in memory as conduction data at 612 for each spatial region. At 614, the graphical map is generated (e.g., by map generator 118) based on the stored conduction data such as demonstrated in connection with FIG. 4.

Figure 7:
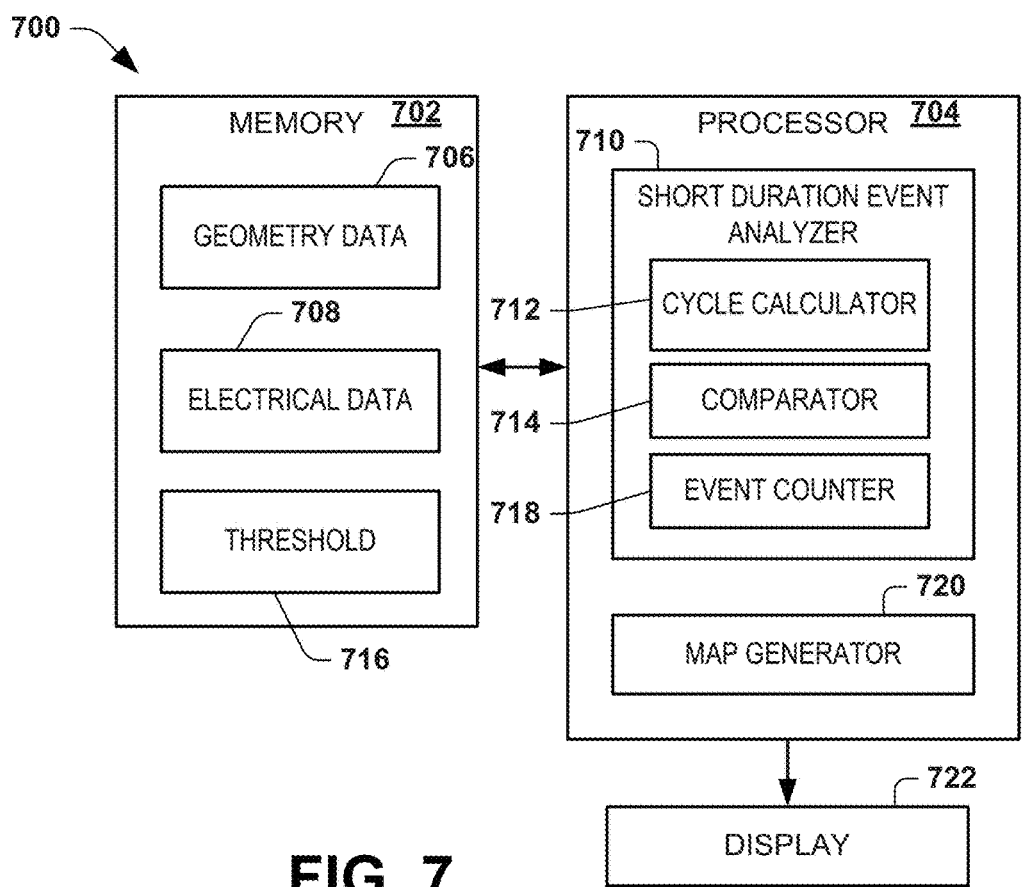
FIG. 7 depicts an example of a system to identify regions exhibiting short duration events.

FIG. 7 depicts an example of a system 700 to determine short duration electrophysiological events, such as corresponding to short fibrillatory cycle length events. The system 700 is demonstrated as a computing apparatus that includes memory 102 and a processor 704. The memory 702 is configured as one or more non-transitory media to store data and instructions. The processor 704 is configured to access the memory and execute the instructions to perform the methods and functions disclosed herein.

The memory 102 stores geometry data 706 and electrical data 708. The electrical data represents electrical signals at plurality of locations (nodes) distributed across a three-dimensional (3D) surface over one or more time intervals. The electrical data 106 may include real-time measurements of the electrical activity and/or previous measurements, which generally may vary depending on whether the system 100 is being utilized for real time analysis (e.g., during an electrophysiological study) or post-procedure analysis. In one example, the electrical data is provided as unipolar electrical signals representing electrical potential across the surface. For example, the electrical potential may be measured directly from nodes across the surface (e.g, a heart or body surface). The measurements may be made using contact or non-contact electrodes distributed across the surface, for example. In another example, the electrical potential across the surface or be reconstructed to nodes distributed across a cardiac surface by solving the inverse problem based electrical signals measured non-invasively from the surface of a patient's body. That is, in one example, the electrical data includes unipolar signals that have been reconstructed onto a surface (e.g, epicardial or endocardial surface) of the heart.

The geometry data 706 represents a 3D surface geometry for the anatomical surface. For example, the anatomical surface may be in the form of a 3D surface mesh, such as including a plurality of nodes that distributed spatially across the surface and are interconnected to adjacent neighboring nodes by an edge of the mesh surface. Thus, the electrical data 708 correspond to electrical signals at each of the plurality of nodes on the surface geometry.

The processor 704 includes a short duration event analyzer 710 programmed to analyze short duration electrophysiological events. The short duration event analyzer 710 is programmed to provide a measure of short duration electrophysiological events that occur across the surface defined by the geometry data 706. In this example, the term short is used to indicate that the measured duration is below an expected duration for this type of electrophysiological event. The event analyzer 710 analyzes fibrillatory signals at each of the plurality of nodes over one or more time intervals. For example, the event analyzer identifies fibrillatory portions of the electrical signals for analysis, namely those portions of the signals not exhibiting a normal (e.g., consistent) sinus rhythm. One or more measurement time intervals for the signals being analyzed may be selected such as to include some fibrillatory signals. For example, the measurement time intervals may be selected in response to user input (e.g., identifying one or measurement time intervals for signal containing fibrillatory activity from signals presented on a graphical user interface), be automatically selected (e.g., by a fibrillation detection algorithm) or include a combination of manually and automatically selected measurement intervals.

A cycle duration calculator 712 is programmed to determine a cycle duration (a cycle length) for each the signals at each of the plurality of nodes for the one or more selected time intervals. The cycle duration calculator 712 may determine the cycle duration for each of the signals by analyzing signal morphology. As an example, the calculator 712 analyzes each of the signals in the selected interval(s) to find (e.g., identify) downward sloping signals segment in each of the signals at each of the plurality nodes. As mentioned, the selected time interval(s) may correspond to an interval exhibiting fibrillatory activity for at least some of the nodes or otherwise be of interest. A morphological signal feature in each of the downward sloping signals is identified. For example, the cycle calculator 712 may identify a peak, a valley, a midpoint or other point along the identified downward sloping segment that may be identified in each such segment. The cycle duration calculator 712 identifies such feature in each of the downward sloping signal segments of each selected signal. The calculator 712 computes the cycle duration as corresponding to the time interval between adjacent identified like features in consecutive downward sloping signal segments for each of the signals. For example, each feature (like each point along the signal) has a time stamp, and the cycle duration is calculated as a difference between a timestamp for the feature of one downward sloping signal segment and the timestamp for the same feature of the adjacent (e.g., either a next or earlier) downward sloping signal segment.

The short duration event analyzer includes a comparator 714 that compares the calculated cycle duration for each of the segments relative to a threshold that is stored in memory at threshold data 716. There may be one or more thresholds, such as to provide a range of shortness. Each threshold may be a fixed parameter or a variable parameter, such as be computed dynamically for a given patient based on analysis of signal activity. As one example, the threshold may be generated based on an average cycle length of the signals across the heart surface over a period of time.

As another example, a sliding window of the average cycle length over a time period (e.g., a sliding one second window) may be chosen for a given fibrillation window. For example, a one second window or other fixed duration may be set as a moving window and a number of short cycle lengths within each one second window can be counted and utilized to normalize the quantity of short cycle lengths. As another example, to mitigate anomalies, the event analyzer 710 can limit the analysis short cycle length to instances where a predetermined number of short cycle lengths occur within a fixed time window or in two or more consecutive cycles. In this way, specificity for the short cycle length detection and analysis may be increased.

The event analyzer 710 also includes an event counter 718 programmed to count the number of short cycle events that occur during a time period (e.g., a fixed or moving time window) for which the analysis is performed. The number of short cycle duration events for each of the plurality nodes can be linked to the nodes programmatically and stored as short duration event data in memory 702. In this way, the short duration events may be evaluated spatially across the surface over one or more time intervals.

A map generator 720 may generate a graphical map based on the short duration event data to visualize the short duration events spatially across a graphical representation of the anatomical surface. As noted, the anatomical surface may correspond to a surface of the heart (e.g., endocardial or epicardial) or it may correspond to a body surface for which the electrical signals are measured. The map generator thus can generate a graphical map of the surface that can be provided to (via an interface—not shown) and visualized on a display 722.

Figure 8:
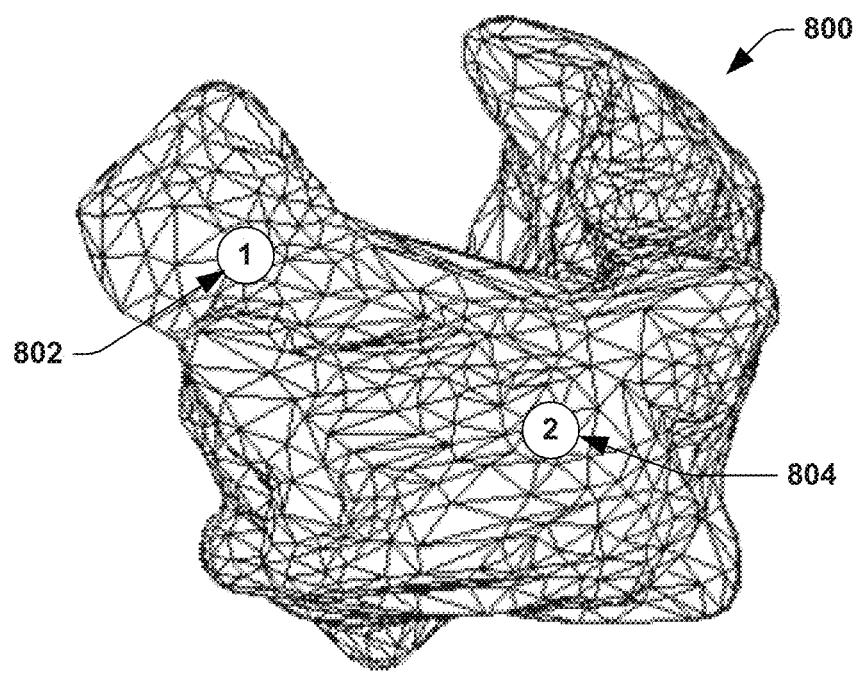
FIG. 8 depicts an example of a mesh of an anatomical surface showing points where measurements are made on the surface.

By way of further example, FIG. 8 depicts a representation of a heart surface demonstrated as a 3D mesh surface (e.g., corresponding to the surface defined by geometry data 706). In this example, a pair of node locations 802 and 804 are shown at spaced apart locations on the heart surface. These two locations 802 and 804 are selected for use in explaining the graphs shown in FIG. 9 and signals from each such location. In other examples, signals may be analyzed for each of the nodes distributed across the surface or to selected regions of the surface (e.g., a selected atrial region or ventricular region).

Figure 9:
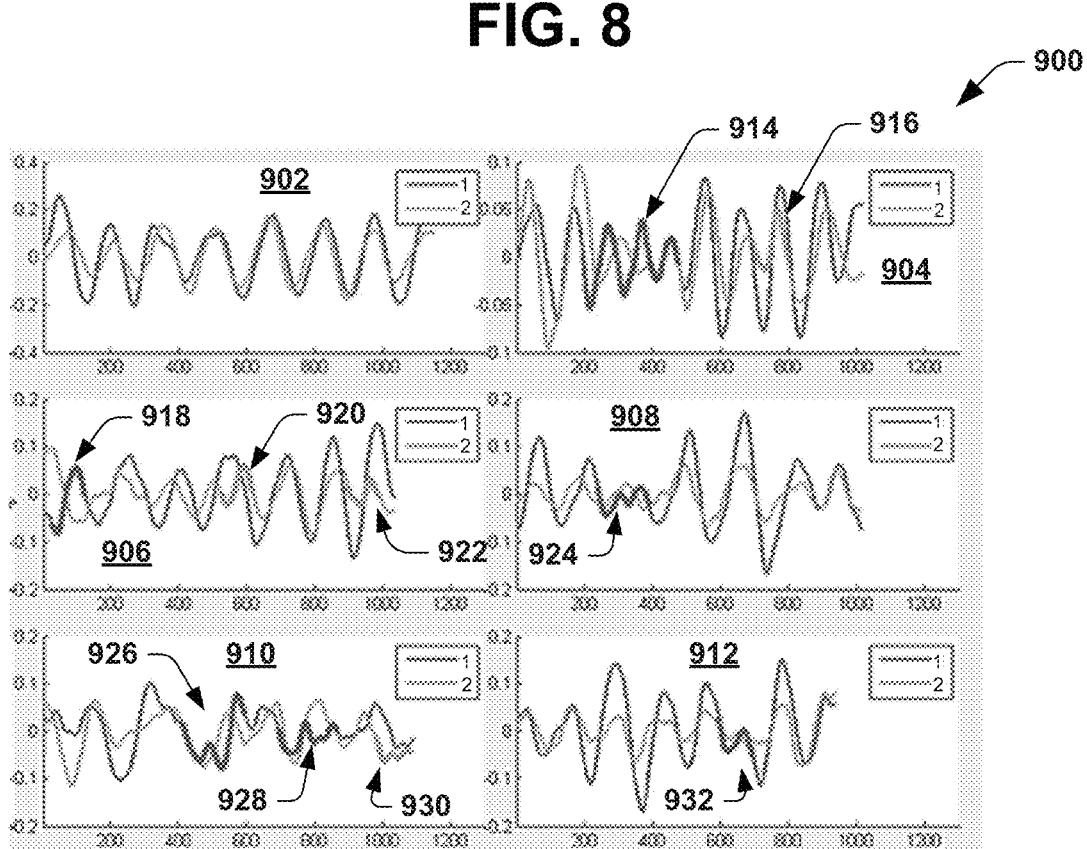
FIG. 9 is a graph showing waveforms for the points of FIG. 8 over a plurality of time intervals.

In FIG. 9, six graphs 902, 904, 906, 908, 910, and 912 are shown for different time intervals. Each of the graphs 902-912 illustrates unipolar signal waveforms for fibrillatory signals at each of the node locations 802 and 804 during respective time intervals. In the example of FIG. 9 waveform 1 corresponds to signal at 802 and the waveform 2 corresponds to signals at 804.

The signal waveforms in graph 902 are shown to demonstrate an absence of short duration events in both waveforms. In each of the other graphs 904-912 one or more of the waveforms exhibit some short duration events, which is visualized by a widening of the waveform line thickness. For example, short duration event in the graph 904 is shown at 914 for 3 consecutive cycles in waveform 1 and at 916 for one cycle in waveform 2. In graph 906, short duration event is shown at 918 for one cycle of waveform 1 and at 920 and 922 for two different cycles of waveform 2. In graph 908, only waveform 1 exhibits short duration event at 924. In graph 910, short duration event is shown at 926 for two cycles of waveform 1, at 928 for two more cycles of waveform 1, and 930 for about one cycle of waveform. Finally, in graph 912, short duration event is shown at 932 for one cycle of waveform 1 and no short duration event in waveform 2.

As explained with respect to FIG. 7, for each of the respective nodes 802 and 804 as well as other nodes distributed across the surface, the number of short duration events can be quantified by the short duration event analyzer 710 over a plurality of intervals, such as those demonstrated in FIG. 9. The map generator 720 thus can employ the resulting measure of short duration events determined across the surface to generate a corresponding short duration event map, which can be provided to a display to visualize regions exhibiting short duration events, such as the graphical map 1000 demonstrated in FIG. 10.

Figure 10:
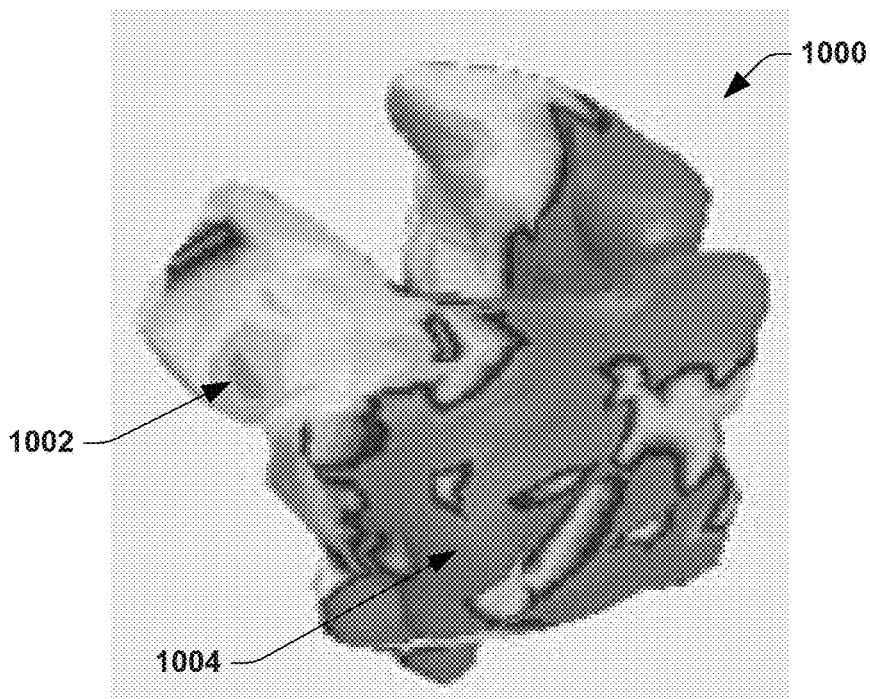
FIG. 10 depicts an example of a graphical map showing regions exhibiting short duration events across a surface.

As shown in FIG. 10, the graphical map 1000 provides a visualization that identifies regions exhibiting short duration events across the surface of the heart, including locations 802 and 804 from FIG. 8. The map 1000 may thus be used to identify one or more regions exhibiting short duration events, such as frequent short fibrillatory cycle lengths. As shown in the graphical map 1000 of FIG. 10, a significant amount of short duration events are demonstrated in the map 1000 at region 1002, corresponding to a location 802 disclosed with respect to FIGS. 8 and 9. However, the location generally corresponding to 804, demonstrated at 1004 in the map 1000 of FIG. 10, does not exhibit any significant quantity short duration events. The region of short duration events at 1002 (as well as other regions exhibiting frequent short duration events) thus may be utilized as target sites for treatment and/or further diagnosis and analysis.

Figure 11:
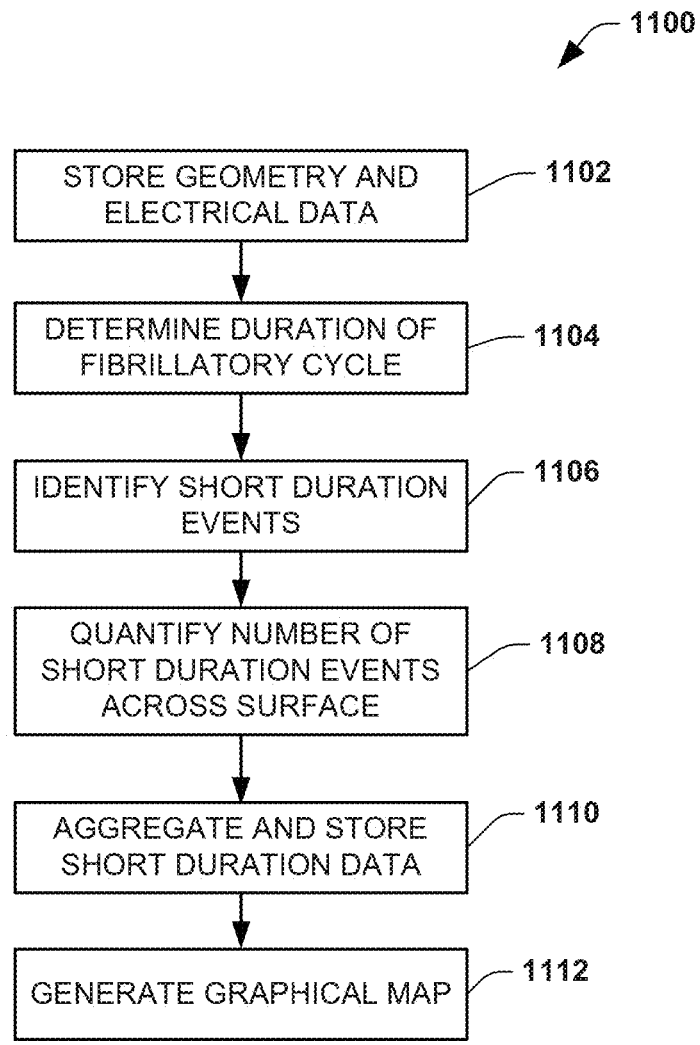
FIG. 11 is a flow diagram illustrating an example method that can be implemented to identify regions exhibiting short duration events.

FIG. 11 is a flow diagram of an example method 1100 for analysis of short duration of electrophysiological events, such as short duration fibrillatory cycle length events. The method 1100 may be implemented by a short duration event analyzer (e.g., event analyzer 710 of FIG. 7). The method begins at 1102 in which geometry and electrical data is stored in memory (e.g., data 706, 708 in memory 702). At 1104, a cycle duration for electrophysiological signals is determined. For example, the cycle duration is determined for one or more intervals of electrical signals at each of a plurality of nodes distributed across a surface (e.g., a 3D surface for which electrical signals are determined, such as the heart or body surface). As mentioned, the electrical signals can correspond to unipolar electrical signals that are either measured directly from the surface or reconstructed onto the surface (e.g., reconstructed electrical potentials across the heart surface).

At 1106, short duration events are identified based on the determined cycle durations (e.g., fibrillatory cycle durations). For example, the short duration events are identified by comparing each cycle duration to a corresponding threshold. As disclosed herein, the threshold may be fixed or vary over time. At 1108, a number of short duration events that occur for each node across the surface are quantified over one or more time intervals. At 1110, the short duration event data is aggregated for each node and stored in memory. Thus, the short duration event data describes a spatial distribution of short duration electrophysiological activity across the surface. At 1112, a corresponding graphical map of the short duration electrophysiological is generated, such as the example map shown in FIG. 10.

Figure 12:
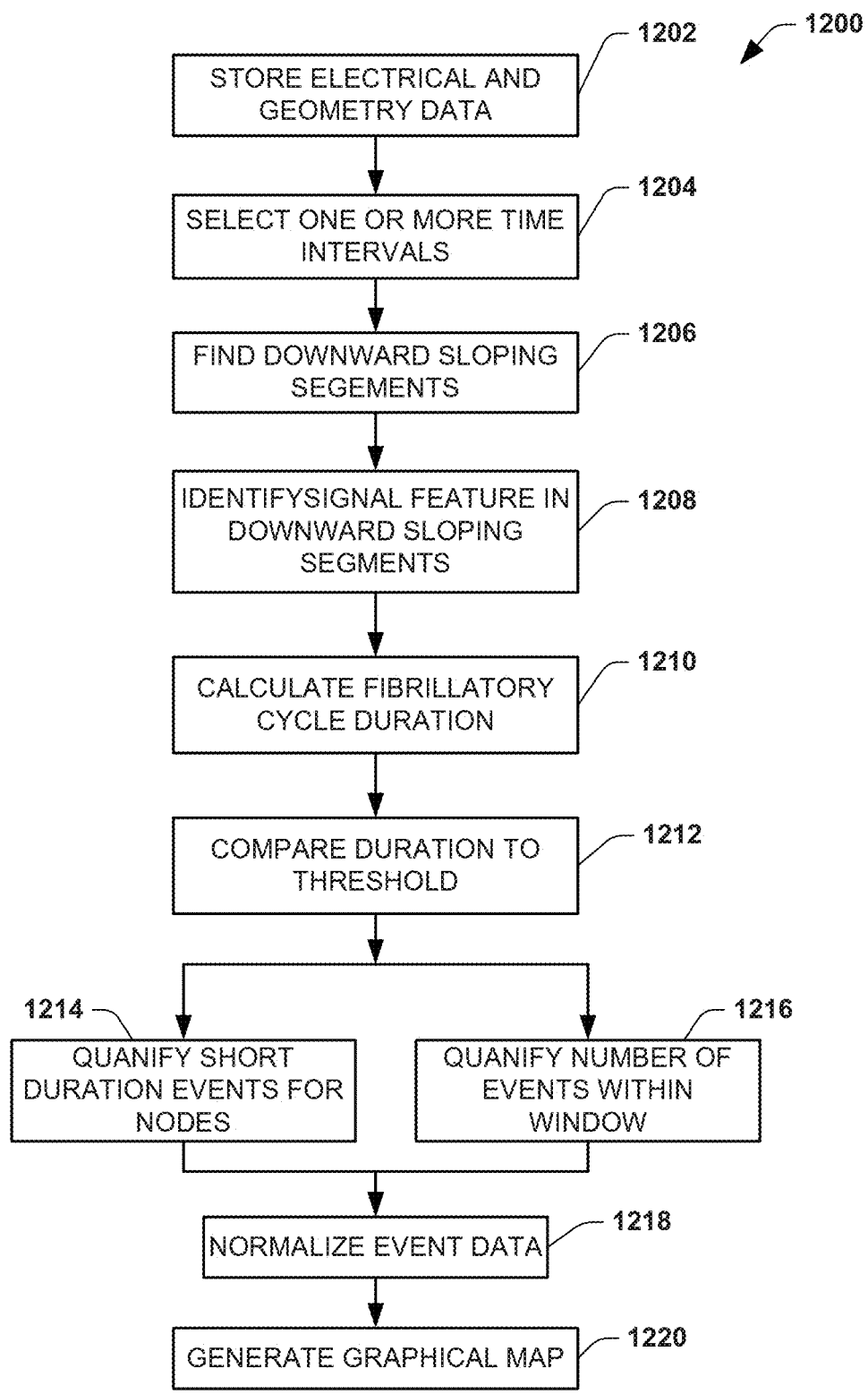
FIG. 12 is a flow diagram illustrating another example method that can be implemented identify regions exhibiting short duration events.

FIG. 12 depicts an example of another method 1200 that can be utilized to provide a spatial measure of short duration electrophysiological events across an anatomical surface. The method 1200, similar to the method 1100, may be implemented by a short duration event analyzer (e.g., event analyzer 710 of FIG. 7). The method 1200 begins at 1202 in which electrical and geometry data is stored (e.g., data 706, 708 in memory 702). At 1204, one or more time intervals are selected from electrical signals (e.g., unipolar electrical potentials across the anatomical surface), such as to include fibrillatory signal activity for at least some of the nodes. For example, the time interval(s) can be selected manually in response to a user input, such as by selecting an interval of a signal waveform (e.g., by selecting a beginning time and end time for the interval) from a graphical user interface that displays signals on the surface of interest. Additionally or alternatively, one or more time intervals can be selected automatically in response to a fibrillatory detection method.

At 1206, the downward sloping segments of each waveform are found in the identified fibrillatory signals. At 1208, a common morphological signal feature (e.g., a peak, valley or an intermediate point thereof) is identified in each of the downward sloping segments. At 1210 a cycle duration is calculated based on the time interval between signal features that have been identified in consecutive downward sloping segments of each of the signal waveforms for each of the nodes distributed across the surface.

At 1212, each of the cycle durations (calculated at 1210) are compared to a threshold to identify short duration electrophysiological events (e.g., by discriminating between short duration cycle lengths and other activity). The threshold may be fixed in some examples. In other examples the threshold may be dynamically calculated. As an example, an average cycle length may be monitored over a sliding window of a certain time length (e.g., about 10 minutes or so), and the threshold for short cycle length can be generated as a percentage of the average cycle length.

In another example, the cycle lengths for the signal waveforms across the surface may be analyzed over a period of time. A histogram of the cycle lengths may be generated from the analysis, and distributions of the cycle lengths may be grouped, such as into one group corresponding to slower cycle lengths and another group corresponding to faster cycle lengths. The different groups may be used to set the threshold, such as by defining the threshold to at a cycle length value that is between the faster group and the slower group. The threshold may be set once or updated periodically based on repeatedly analysis the signal waveforms using a sliding window of time as the analysis period of time.

Based on the comparison and threshold applied to 1212, the short duration of events that occur across the surface are quantified. For example, at 1214, short duration of events for nodes can be quantified by counting the total number of short duration of events that occur over the one or more time intervals. Alternatively or additionally, at 1216, the number of events within a given time window may be quantified. For example, the number of short duration of events that occur within a moving time window (e.g., 1000 ms, another period of time or a predetermined number of time samples) may be determined to quantify events for each time window. The moving window of quantified events also may be stored in memory.

At 1218, the quantified number of events may be normalized. For example, the number of short duration events may be normalized over the aggregate time period (e.g., including one or more time intervals) for which the short duration of events have been counted and quantified (e.g., at 1214 and/or 1216). At 1220, a graphical map can be generated based on the normalized event data. In other examples, the quantified number of short duration of events, as determined at 1214 and/or 1216, may be utilized (e.g., by map generator 720) to generate the graphical map at 1220.

Figure 13:
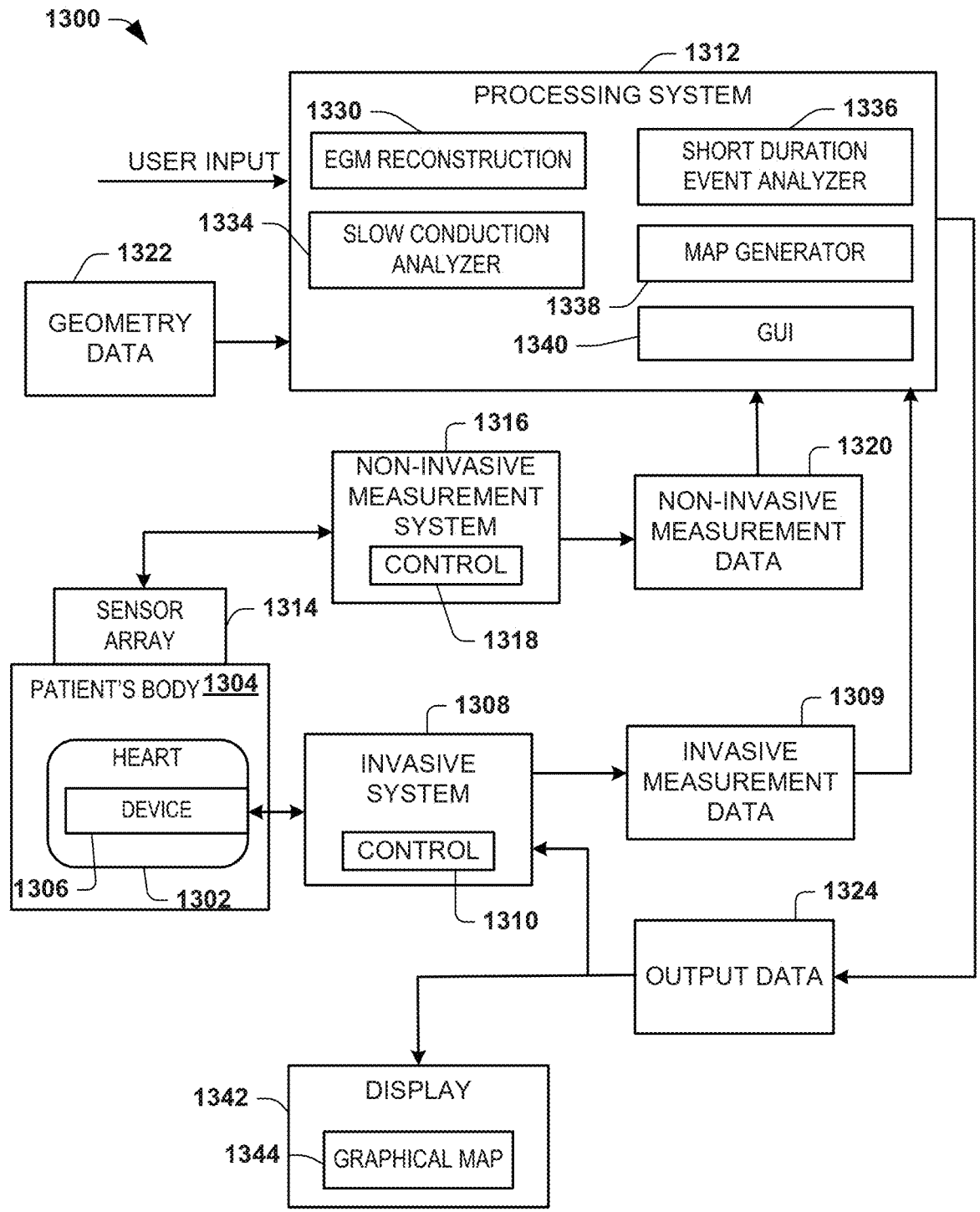
FIG. 13 depicts an example system that can be used for diagnosis and/or treatment.

FIG. 13 depicts an example of a system 1300 that can be utilized for performing diagnostics and/or treatment of a patient. In some examples, the system 1300 can be implemented to generate corresponding graphical outputs for signals and/or graphical maps for a patient's heart 1302 in real time as part of a diagnostic procedure (e.g., monitoring of signals during an electrophysiology study) to help identify irregular electrophysiological activity for the patient's heart (e.g., including slow conduction velocity and/or short events), such as disclosed herein. Additionally or alternatively, the system 1300 can be utilized as part of a treatment procedure, such as to help a physician determine parameters for delivering a therapy (e.g., delivery location, amount and type of therapy) based on one or more regions of irregular electrophysiological activity identified for the patient's heart.

As one example, an invasive device 1306, such as a pacing catheter, having one or more electrodes affixed thereto can be inserted into a patient's body 1304. The electrode can contact or not contact the patient's heart 1302, endocardially or epicardially. The placement of the device 1306 can be guided via a localization method, which can operate to localize the device 1306. The guidance can be automated, semi-automated or be manually implemented based on information provided. Those skilled in the art will understand and appreciate various type and configurations of devices 1306, which can vary depending on the type of treatment and the procedure.

For example, the device 1306 can include one or more electrodes disposed thereon at predetermined locations with respect to the device. Each such electrode can be positioned with respect to the heart 1302 via the device 1306 and apply an electrical signal (e.g., a waveform) that can be measured by a plurality of sensors (e.g., in non-invasive sensor array 1314 or another invasive device 1306) located at known locations in a three-dimensional coordinate system. The sensors thus can sense electrical activity corresponding to each applied signal. The sensors can also sense other electrical signals, such as corresponding to unipolar electrograms (e.g., electrical potential) measured for the patient's heart 1302. An invasive system 1308 can include a control 1310 configured to process (electrically) and control the capture of the measured signals as to provide corresponding invasive measurement data 1309.

By way of example, the device 1306 can be configured to deliver an electrical signal. The device 1306 can apply the signal as to deliver a prescribed therapy, such as ablation, a pacing signal or to deliver another therapy (e.g., providing electrical therapy, or controlling delivery of chemical therapy, sound wave therapy, or any combination thereof). For instance, the device 1306 can include one or more electrodes located at a tip of a pacing catheter, such as for pacing the heart, in response to electrical signals (e.g., pacing pulses) supplied by the system 1308. Other types of therapy can also be delivered via the system 1308 and the device 1306 that is positioned within the body. The therapy delivery means can be on the same catheter or a different catheter probe than is used for sensing electrical activity.

As a further example, the system 1308 can be located external to the patient's body 1304 and be configured to control therapy that is being delivered by the device 1306. For instance, the system 1308 can also control electrical signals provided via a conductive link electrically connected between the delivery device (e.g., one or more electrodes) 1306 and the system 1308. The control system 1310 can control parameters of the signals supplied to the device 1306 (e.g., current, voltage, repetition rate, trigger delay, sensing trigger amplitude) for delivering therapy (e.g., ablation or stimulation) via the electrode(s) on the invasive device 1306 to one or more location on or inside the heart 1302. The control circuitry 1310 can set the therapy parameters and apply stimulation or other therapy based on automatic, manual (e.g., user input) or a combination of automatic and manual (e.g., semiautomatic) controls. One or more sensors (not shown but could be part of the device) can also communicate sensor information back to the control 1310. The control can be based on irregular electrophysiological activity identified (e.g., by the processing system 1312) for one or more spatial region of the patient's heart 1302.

Before, during and/or after delivering a therapy to the patient 1304 (e.g., via the system 1308), one or more of the systems 1308 or 1316 can be utilized to acquire electrophysiology information for the patient. In the example of FIG. 13, a sensor array 1314 includes one or more sensors that can be utilized non-invasively for measuring patient electrical activity. As one example, the sensor array 1314 can correspond to a high-density arrangement of body surface sensors that are distributed over a portion of the patient's outer body surface (e.g., thorax) for measuring electrical activity associated with the patient's heart (e.g., as part of an electrocardiographic mapping procedure).

Examples of the non-invasive sensor array 1314 that can be employed to measure body surface electrical activity are shown and described in U.S. Pat. No. 9,655,561, which was filed Dec. 22, 2011, and International patent application No. PCT/US2009/063803, which was filed Nov. 10, 2009, each of which applications is incorporated herein by reference. Other arrangements and numbers of sensors can be used as the sensor array 1314. For example, the array can be a reduced set of sensors, which does not cover the patient's entire torso and is designed for measuring electrical activity for a particular spatial region (e.g., an arrangement of electrodes specially designed for analyzing atrial and/or ventricular activity).

The electrical signals (e.g., potentials) measured non-invasively via the array 1314 are provided to the measurement system 1316. The measurement system 1316 can include appropriate controls and signal processing circuitry 1318 for providing corresponding measurement data 1320 that describes electrical activity measured by the electrodes in the sensor array 1314. The measurement data 1320 can include analog and/or digital information (e.g., corresponding to electrical data 106, 708).

The non-invasive measurement control 1318 can also be configured to control the data acquisition process (e.g., sample rate, line filtering) for measuring electrical activity and providing the non-invasive measurement data 1320. For example, the non-invasive measurement data may represent unipolar electrical potential measured across the surface of the patient's body according to the position of the electrodes in the array 1314. In some examples, the control 1318 can control acquisition of measurement data 1320 separately from the therapy system operation, such as in response to a user input. In other examples, the measurement data 1320 can be acquired concurrently with and in synchronization with delivering therapy, such as to detect electrical activity of the heart 1302 that occurs in response to applying a given therapy (e.g., according to therapy parameters).

In some examples, the processing system 1312 includes an electrogram reconstruction method 1330, which is programmed to reconstruct electrical activity on a cardiac envelope (e.g., a surface of the patient's heart). For example, the reconstruction method 1330 is programmed to solve an inverse problem to estimate corresponding reconstructed electrograms, corresponding to unipolar electrical signals across the cardiac envelope. The reconstruction method 1330 thus can reconstruct the body surface electrical activity measured via the sensor array 1314 onto a multitude of nodes distributed across the cardiac envelope (e.g., 3D surface with nodes at 100 locations, greater than 1000 locations, such as about 2000 locations or more). Examples of computations that the electrogram reconstruction method 1330 may implement to reconstruct the electrical activity on the cardiac envelope are described in U.S. Pat. No. 6,772,004 and in U.S. Pat. No. 7,983,743, each of which is disclosed herein by reference in its entirety.

Since, in some examples, the measurement system 1316 can measure electrical activity of a predetermined region or the entire heart concurrently (e.g., where the sensor array 1314 covers the entire thorax of the patient's body 1304), the accuracy in the resulting output data 1324, which can include specifying regions of irregular electrophysiological activity, can be increased when compared to other approaches, such as to supply the user with a more accurate and global information to facilitate monitoring and application of therapy. Additionally or alternatively, the localization can be continuous process and/or be synchronized with respect to the application of therapy provided by the system 1308.

As disclosed herein, the cardiac envelope can correspond to a 3D surface geometry corresponding to a patient's heart, which surface can be epicardial and/or endocardial. Alternatively or additionally, the cardiac envelope can correspond to a geometric surface that resides between the epicardial surface of a patient's heart and the surface of the patient's body where the sensor array 1314 has been positioned. Additionally, the geometry data 1322 that is utilized by the electrogram reconstruction 1330 can correspond to actual patient anatomical geometry, a preprogrammed generic model or a combination thereof (e.g., a model that is modified based on patient anatomy).

As an example, the geometry data 1322 may be in the form of graphical representation of the patient's torso, such as derived from processing image data acquired for the patient. Such image processing can include extraction and segmentation of anatomical features, including one or more organs and other structures, from a digital image set. Additionally, a location for each of the electrodes in the sensor array 1314 can be included in the geometry data 1322, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array in the coordinate system, such as a digitizer or manual measurements. As mentioned above, the geometry data 1322 can correspond to a mathematical model, such as can be a generic model or a model that has been constructed based on image data for the patient.

In the example of FIG. 13, the processing system also includes a slow conduction analyzer 1334 and a short duration event analyzer 1336. The slow conduction analyzer may correspond to the conduction velocity analyzer 112, 200 disclosed herein, such as to perform the method of FIGS. 5 and/or 6. The short duration event analyzer may correspond to the short duration event analyzer 710, such as to perform the method of FIGS. 11 and/or 12. Accordingly, reference may be made back to corresponding portions of the description for additional information about the slow conduction analyzer 1334 and short duration event analyzer 1336.

A map generator 1338 can generate corresponding output data 1324 based on slow conduction data generated by the slow conduction analyzer 1334. Additionally or alternatively, the map generator 1338 can generate the output data 1324 based on short duration event data determined by the short duration event analyzer 1336. The output data 1324 may, in turn, be rendered as a corresponding graphical map 1344 in a display 1342. For example, the graphical map 1344 may include a slow conduction map to identify one or more spatial regions of the heart that exhibit slow conduction velocity (see, e.g., FIG. 4). As another example, the graphical map 1344 may include a short duration map to identify one or more spatial regions of the heart that exhibit frequent short fibrillatory cycle lengths (see, e.g., FIG. 10).

Additionally, in some examples, the output data 1324 can be utilized by the system 1308 in connection with controlling delivery of therapy or monitoring electrical characteristics. The control 1310 that is implemented can be fully automated control, semi-automated control (partially automated and responsive to a user input) or manual control based on the output data 1324. In some examples, the control 1310 of the therapy system can utilize the output data (e.g., specifying one or more regions of slow conduction velocity and/or regions of short duration fibrillatory cycle length) to control one or more therapy parameters. In other examples, an individual can view the map 1344 generated on the display 1342 to manually control the system 1308. Other types of therapy and devices can also be controlled based on the output data 1324 and corresponding graphical map 1344.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. One or more non-transitory computer-readable media having instructions executable by a processor, the instructions programmed to perform a method comprising:
    defining a plurality of spatial regions distributed across a three-dimensional geometric surface corresponding to a heart of a patient;
    detecting at least one wave front that propagates across the three-dimensional geometric surface based on electrical data representing electrophysiological signals for each of a plurality of nodes distributed on the three-dimensional geometric surface over at least one time interval;
    determining a duration that the wave front resides within at least one spatial region of the plurality of spatial regions during the at least one time interval;
    identifying slow conduction activity for the at least one spatial region based on comparing the duration that the wave front resides within the at least one spatial region relative to a duration threshold; and
    storing in memory conduction data representing the slow conduction activity identified for each spatial region.

2. The media of claim 1, wherein the method further comprises generating a graphical map visualizing each region exhibiting slow conduction activity during the at least one time interval on a graphical representation of the three-dimensional geometric surface corresponding to anatomy of the heart based on the conduction data.

3. The media of claim 1, wherein each of the plurality of spatial regions is defined to includes a set of the nodes residing within a predetermined spatial distance from a respective one of the plurality of nodes.

4. The media of claim 3, wherein each of the plurality of spatial regions is defined as a circular region centered around the respective node and having a predetermined diameter that is twice the predetermined spatial distance.

5. The media of claim 3, wherein the slow conduction activity for the at least one spatial region is further determined based on the predetermined spatial distance.

6. The media of claim 1, wherein detecting the at least one wave front further comprises detecting each of a plurality of wave fronts that propagate across the three-dimensional geometric surface based on the electrical data, the method further comprising:
    determining a duration that each wave front of the plurality of wave fronts resides within a respective spatial region of the plurality of spatial regions over the at least one time interval; and
    identifying slow conduction activity for each of the plurality of spatial regions based on a comparing the duration that each wave front resides within the respective spatial region relative to the duration threshold; and
    storing the conduction data in the memory to represent the slow conduction activity identified for each of the plurality of spatial regions.

7. The media of claim 6, wherein the method further comprises quantifying a relative amount of slow conduction activity for each of the plurality of regions.

8. The media of claim 6, wherein determining the duration that each wave front resides within the respective spatial region further comprises:
    determining the duration that a given wave front of the plurality of wave fronts resides in each of the plurality of spatial regions;
    weighting each of the plurality of spatial regions according to an amount of time that the determined duration for the given wave front exceeds the duration threshold for that region;
    repeating the determining and weighting for each remaining wave front of the plurality of wave fronts; and
    aggregating the weighting for each of the plurality of spatial regions, such that the aggregated weighting quantifies a relative amount of slow conduction activity for each of the plurality of regions.

9. The media of claim 8, wherein the method further comprises generating a graphical map visualizing the relative amount of slow conduction activity for each of the plurality of regions based on the conduction data.

10. The media of claim 1, wherein the duration that the wave front resides within the at least one spatial region is a continuous duration of consecutive time frames within the at least one time interval.

11. The media of claim 1, wherein the duration threshold is programmable in response to a user input instruction.

12. The media of claim 1, wherein the electrophysiological signals at each of the plurality of nodes over the at least one time interval comprise unipolar signals on a body surface of the heart reconstructed from body surface electrophysiological signals measured non-invasively from the body surface.

13. The media of claim 1, wherein the at least one time interval is selected, such that the electrophysiological signals include fibrillatory signals, the method further comprises:

determining a cycle duration for the electrophysiological signals at each of the plurality of nodes over the at least one time interval;

comparing each cycle duration to a short duration threshold to identify each short duration event for each electrophysiological signal;

quantifying a number of short duration events at each of the plurality of nodes that occur during the at least one time interval; and generating a graphical map visualizing the number of short duration events that occur across a graphical representation of the heart.

14. The media of claim 13, wherein determining the cycle duration further comprises:

finding downward sloping signal segments for each of the electrophysiological signals at each of the plurality of nodes over the at least one time interval;

identifying a feature in each of the downward sloping signal segments; and calculating the cycle duration as a corresponding time interval between the feature in consecutive the downward sloping signal segments for each of the electrophysiological signals.

15. A system comprising:

memory to store machine readable instructions and data, the data comprising electrical data representing electrophysiological signals for a plurality of nodes distributed across a geometric surface over at least one time interval;

at least one processor to access the memory and execute the instructions, the instructions comprising:

code to detect at least one wave front that propagates across the geometric surface based on the electrical data, the geometric surface including a plurality of spatial regions;

code to determine a duration that the at least one wave front resides within at least one spatial region of the plurality of spatial regions during the at least one time interval;

code to identify slow conduction activity for the at least one spatial region based on the duration that the at least one wave front resides within the at least one spatial region being less than a duration threshold; and code to store in the memory conduction data to represent slow conduction activity for each of the plurality of spatial regions.

16. The system of claim 15, wherein the instructions further comprises code to generate a graphical map visualizing an extent to which each region exhibits slow conduction events during the at least one time interval on a graphical representation of the geometric surface corresponding to the heart based on the conduction data.

17. The system of claim 15, wherein each of the plurality of spatial regions includes a set of the nodes residing within a predetermined spatial distance from a respective node of the plurality of nodes.

18. The system of claim 17, wherein each of the plurality of spatial regions is defined as a circular region centered around the respective node and having a predetermined diameter that is twice the predetermined spatial distance.

19. The system of claim 17, wherein the slow conduction activity for the at least one spatial region is further determined based on the predetermined spatial distance and the duration that at least a portion of the at least one wave front is continuously residing within the predetermined spatial distance of the respective node.

20. The system of claim 15, wherein the code to detect the at least one wave front further comprises code to detecting each of a plurality of wave fronts that propagate across the geometric surface based on the electrical data, the instructions further comprising:

code to determine a duration that each wave front of the plurality of wave fronts resides within a respective spatial region of the plurality of spatial regions during the at least one time interval; and code to identify slow conduction events corresponding to slow conduction activities for each of the plurality of spatial regions based on the duration that each wave front resides within the respective spatial region being less than the duration threshold, wherein the conduction data represents each slow conduction event for each of the plurality of spatial regions.

21. The system of claim 20, wherein the code to determine the duration that each wave front resides within the respective spatial region comprises:

code to determine the duration that a given wave front of the plurality of wave fronts resides in each of the plurality of spatial regions;

code to weight each of the plurality of spatial regions according to an amount of time that the determined duration for the given wave front exceeds the threshold for the respective region;

code to repeat execution of the code to determine and weight for each remaining wave front of the plurality of wave fronts;

code to aggregate the weighting for each of the plurality of wave fronts in the plurality of spatial regions, such that the aggregate weighting quantifies a relative amount of slow conduction activity for each of the plurality of spatial regions; and code to generate a graphical map visualizing the relative amount of slow conduction activity for each of the plurality of regions based on the conduction data.

22. The system of claim 15, further comprising a plurality of electrodes to non-invasively measure the electrophysiological signals from a body surface, wherein the electrophysiological signals at each of the plurality of nodes over the at least one time interval are unipolar signals reconstructed from the non-invasively measured electrophysiological signals.

23. The system of claim 15, the instructions further comprise:

code to select the at least one time interval, such that the electrophysiological signals at least some of the plurality of nodes include fibrillatory signals;

code to determine a cycle duration for the electrophysiological signals at each of the plurality of nodes over the at least one time interval;

code to compare each cycle duration to a duration threshold to identify each short duration event for each the electrophysiological signals;

code to quantify a number of short duration events at each of the plurality of nodes that occur during the at least one time interval; and code to generate a graphical map visualizing the number of short duration events that occur across a graphical representation of a heart.

24. The system of claim 23, wherein the code to determine a fibrillatory cycle duration further comprises:

code to find downward sloping signal segments for each of the electrophysiological signals at each of the plurality of nodes over the at least one time interval;

code to identify a feature in each of the downward sloping signal segments; and code to calculate the cycle duration as the time interval between the feature identified in consecutive the downward sloping signal segments for each of the electrophysiological signals.

25. The system of claim 23, further comprises a therapy system to control delivery of a therapy to a patient based on at least one of the number of short duration events or the conduction data.

26. One or more non-transitory computer-readable media having instructions executable by a processor, the instructions programmed to perform a method comprising:

determining a cycle duration for each of a plurality of electrophysiological signals at each of a plurality of nodes distributed across an anatomical surface for at least one time interval;

comparing each cycle duration to at least one threshold to identify each short duration event for each of the plurality of electrophysiological signals that is less than the at least one threshold;

quantifying a number of short duration events at each of the plurality of nodes that occur during the at least one time interval; and generating a graphical map to display the number of short duration events that occur spatially across a graphical representation of the anatomical surface.

27. The media of claim 26, wherein the at least one time interval is selected, such that the plurality of electrophysiological signals include fibrillatory signals for at least some of the plurality of nodes, wherein determining the cycle duration further comprises:

finding downward sloping signal segments for each of the plurality of electrophysiological signals at each of the plurality of nodes over the at least one time interval;

identifying a morphological signal feature in each of the downward sloping signal segments; and calculating the cycle duration as the time interval between the feature in consecutive the downward sloping signal segments for each of the plurality of electrophysiological signals.

28. The media of claim 26, wherein the threshold is dynamically adjusted over time.

29. The media of claim 26, wherein the method further comprises:

defining a plurality of spatial regions distributed across the anatomical surface;

detecting at least one wave front that propagates across the anatomical surface based on the plurality of electrophysiological signals for each of the plurality of nodes over the at least one time interval;

determining a duration that the at least one wave front resides within at least one spatial region of the plurality of spatial regions during the at least one time interval; and identifying slow conduction activity for the at least one spatial region based on comparing the duration that the wave front resides within the at least one spatial region relative to a slow conduction threshold; and storing in memory conduction data representing the slow conduction activity.

30. A system comprising:

memory to store machine readable instructions and data, the data comprising electrical data representing electrophysiological signals for a plurality of nodes distributed across an anatomical surface over at least one time interval;

at least one processor to access the memory and execute the instructions, the instructions comprising:

code to select at least one measurement time interval, such that the electrophysiological signals for at least some of the plurality of nodes include fibrillatory signals;

code to determine a cycle duration for each of the electrophysiological signals at each of the plurality of nodes over the at least one measurement time interval;

code to compare each cycle duration to a threshold to identify short duration events for each the electrophysiological signals that is less than the threshold;

code to quantify a number of short duration events at each of the plurality of nodes that occur during the at least one measurement time interval; and code to generate a graphical map visualizing the number of short duration events across a graphical representation of the anatomical surface.

* * * * *